(12) United States Patent
Jusinski

(10) Patent No.: US 6,779,218 B1  
(45) Date of Patent: Aug. 24, 2004

(54) APPARATUS AND METHOD FOR ERGONOMIC BASIC CHIROPODY

(76) Inventor: Robert Jusinski, 1761 W. Campbell Ave., Campbell, CA (US) 95008

( * ) Notice: Subject to any disclaimer, the term of this patent is extended or adjusted under 35 U.S.C. 154(b) by 315 days.

(21) Appl. No.: 09/802,699

(22) Filed: Mar. 8, 2001

Related U.S. Application Data

(60) Provisional application No. 60/188,326, filed on Mar. 9, 2000.

(51) Int. Cl.[7] .............................................. A46B 11/02
(52) U.S. Cl. ...................... 15/104.92; 15/114; 15/160; 15/216
(58) Field of Search ............................. 15/104.92, 114, 15/118, 110, 160, 161, 216, 215, 217; 4/606; 601/136; D28/63; D4/130

(56) References Cited

U.S. PATENT DOCUMENTS

| | | | |
|---|---|---|---|
| D116,272 S | * 8/1939 | McKeen | D4/116 |
| 5,163,200 A | * 11/1992 | Carlin et al. | 15/104.92 |
| 5,173,972 A | 12/1992 | Goodman | 4/494 |
| 5,177,829 A | 1/1993 | Simpson | 15/104.92 |
| 5,473,788 A | * 12/1995 | Aragona | 15/104.92 |
| 5,678,259 A | 10/1997 | Cruz Jr. | 4/622 |
| 5,724,695 A | 3/1998 | Galizia | 15/160 |
| 5,729,858 A | 3/1998 | Riffel | 815/111 |
| 5,813,078 A | 9/1998 | Hogan, Sr. | 15/160 |
| 5,896,613 A | * 4/1999 | Courtney et al. | 15/119.2 |
| 6,210,350 B1 | * 4/2001 | Finch | 601/136 |
| 6,253,407 B1 | * 7/2001 | Bjelkevig | 15/160 |
| 6,405,400 B1 | * 6/2002 | McClain | 15/160 |

* cited by examiner

Primary Examiner—Theresa T. Snider  
(74) Attorney, Agent, or Firm—Lumen Intellectual Property Services, Inc.

(57) ABSTRACT

A basic chiropody apparatus having a soaping device, a scrubbing device and a brushing device ergonomically shaped and positioned relative to each other in a compact fashion on a triangular base. The apparatus is configured in order to be placed on the floor and in the corner of two walls. As a result, a person operating the apparatus is able to hold itself in a stable position with its arms in perpendicularly pressing against the two walls. The triangular shape of the apparatus provides for a simple repositioning of it in cases where it gets unintentionally replaced during its operation due to wet and soapy floor condition as they may exist in a shower cabin.

5 Claims, 4 Drawing Sheets

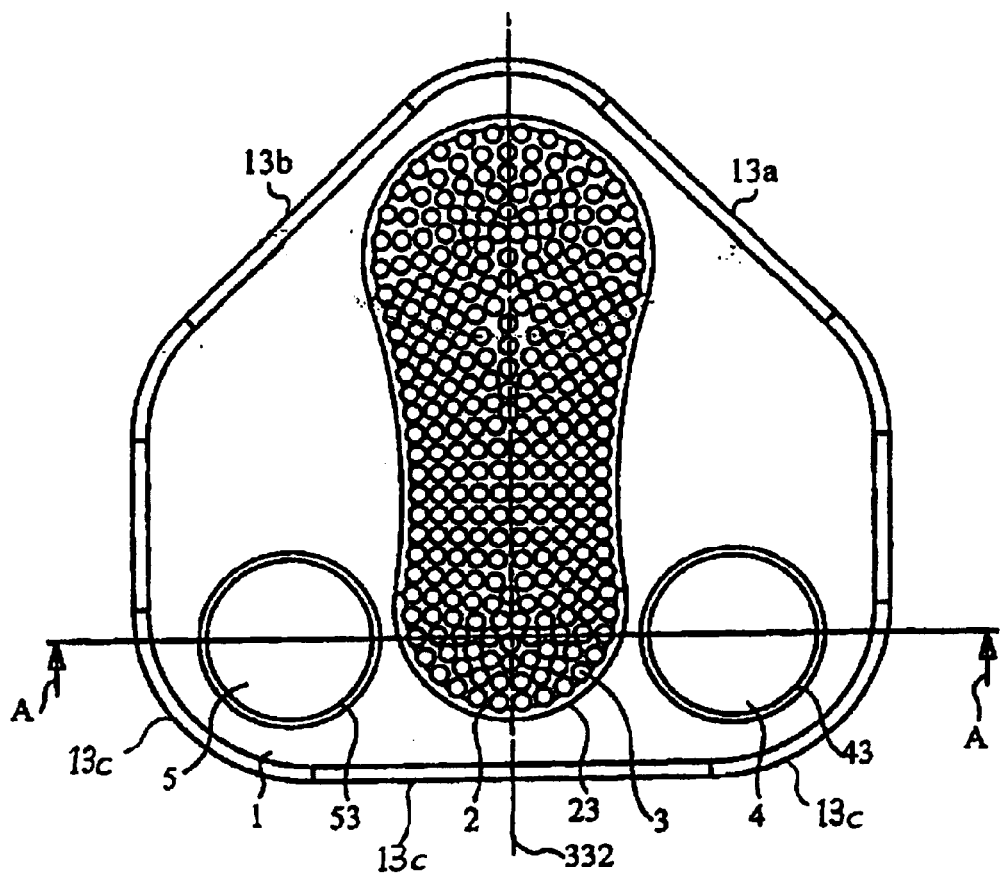
Fig. 2
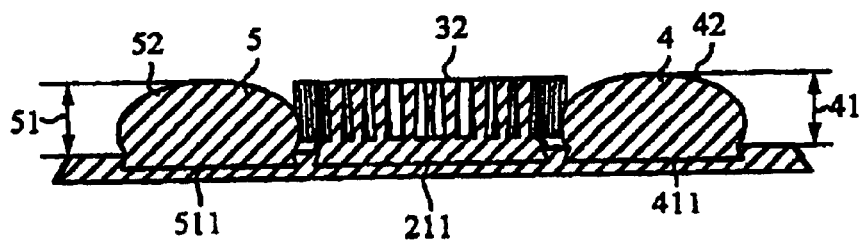
Fig. AA

APPARATUS AND METHOD FOR ERGONOMIC BASIC CHIROPODY

RELATED APPLICATION

The present application claims priority of the provisional U.S. application No. 60/188,326 filed Mar. 9, 2000, which is hereby incorporated by reference.

BACKGROUND OF INVENTION

Self-performed basic chiropody usually takes place in a bath tub or a shower cabin. The dimensional configuration of shower cabins makes it often difficult to access one's own feet for the purpose of cleaning them. The person attempting to do so has either to balance on one foot while lifting the other foot into reach of his/her hands or has to sit down in the shower cabin. Both tasks are difficult to accomplish. A number of inventions provide more or less suitable apparatus to assist a person cleaning his/her feet.

For example, U.S. Pat. No. 5,321,867 discloses a u-shaped apparatus with a number of brushes mounted on the inside bottom and side walls. The invention is held in place solely by its weight. Lateral pressure against the wall mounted brushes may cause the apparatus to slide or even tilt. The shape of the u-shaped apparatus is sharp edged and clumsy and may not be feasible to be safely placed in a shower cabin.

U.S. Pat. Nos. 5,177,829; 5,678,259 and 5,724,695 disclose foot washing boxes with a number of compartment or features therein that are configured for separate foot cleaning operations. The box shapes are clumsy and do not take into account the limited space within a shower cabin.

U.S. Pat. Nos. 5,173,972; 5,813,078 and 5,729,858 disclose foot washer platforms with one or more cleaning features placed on it or integrated in it. The platform is held in place by a number of suction cups. Suction cups tend to slide on the wet and eventual soapy floor of a shower floor. The shape of the platform does not take into account the space limitations of a shower cabin floor.

The patents cited above are selected in order to give some examples of all the foot washing apparatus that have been invented. All inventions have dimensional configurations that does not take into account the limitation of the location where they intend to be placed. Hence, there exists a need for a simple foot washing apparatus that is ergonomically designed and configured to be placed in a secured position within limited available space like, for example, within a shower cabin.

SUMMARY

A cleaning apparatus is configured to provide access for a soap, a pumice and a brush in an ergonomic fashion such that a person can perform basic chiropody in a stable and upright standing position. The cleaning apparatus, with its functional elements, is specifically configured in order to be placed and operated in a corner defined by two essentially perpendicular walls like, for example, of a bathroom or a shower cabin.

A human's foot movements are naturally mainly performed in forward and backward direction and the correspondingly used joints, tendons and muscles of a human's leg are particularly evolved to perform this movements more easily than lateral foot movements. Hence, when a person attempts to perform a foot cleaning operation, it naturally intends to rub the foot against an obstacle in forward and backward movements. The foot is thereby twisted around the ankle in order to bring the side of the foot, the heel and/or the toes into rubbing contact with the obstacle. The present invention takes advantage of these kinematical predispositions of the human leg and foot and provides the chiropody features in a compact and specifically configured shape and position to each other such that the tasks of soaping, scrubbing and/or brushing can be performed with greatest ease and safety. The soap and the pumice have a compact and smooth shape significantly rising above the main platform of the apparatus, since they have to access also the upper side of the foot. The brush on the other side, which mainly has to access the bottom of the foot extends across a relatively large area of the base in order to provide snuggly contact with the bottom of the foot while it is moved along the brush.

In the preferred embodiment, the soap and the pumice have identical and rotationally symmetric shape such that they can be easily and exchangeable fixated by snapping them into corresponding material separations of the base. They are positioned lateral of the brush such that the three chiropody features occupy a triangular area of the base. The configuration and positioning of the individual features relative to each other results in a compact triangular shape the whole apparatus, which occupies very limited space. The triangular arrangement of soaping device, scrubbing device and brushing device correspond to a triangular shape of the whole apparatus such that the apparatus may be placed in a stable fashion on the floor in the corner between two walls.

Basic chiropody has to be performed with wet feet, which may cause a slippery and unstable contact with the foot holding the persons weight while the other foot is moved more or less dynamically along the individual chiropody devices. The positioning of the apparatus in the corner of two walls allows a person to support itself in a stable fashion with its hands on the two walls while operating the apparatus. The single foot forms thereby with the two hands perpendicular pressing against each of the walls a stable force triangle.

The base itself is preferably of an elastic, rubber-like material that snuggly contacts the floor. The bottom of the base may feature additionally specifically formed cavities that operate as suction cups in order to increase the friction contact with the floor. Since sliding on wet and soapy surfaces as they exist especially in shower cabins cannot be fully prevented, the triangular shape of the base allows an easy repositioning and/or reorienting of the apparatus in cases where it is removed by the movements of the foot to be cleaned. The base is configured such that the foot carrying the person's weight may be placed in contact with a contacting edge and thereby fixating the apparatus in its position.

All chiropody devices can be easily removed from the base for cleaning and replacement. The apparatus is simple to fabricate, easy and safe to use.

The soaping device may be a solid soap or a sponge like device on which a detergent is applied immediately prior to performing the chiropody. The sponge like device may also be impregnated with a detergent in a fashion that only a combination of water and mechanical contact excerpted by the foot to be cleaned releases the detergent to the surface of the sponge device.

The pumice device may have a homogeneous structure or may be made in combination with a different material or may be made completely of a different material configured to perform an abrasion of horny skin.

The brushing device may be made solely of brushed forming a planar surface and/or curved surface(s) configured to brush specific foot areas like, for example, the foot palm and/or the toe region. The brushing device may further include features configured for massaging the bottom of the foot rather than brushing it as are well known to those skilled in the art.

BRIEF DESCRIPTION OF FIGURES

FIG. 2 shows a top down view of the present invention.

FIG. AA shows a sectional view of the present invention along a section line A—A indicated in FIG. 2.

Figure 3:
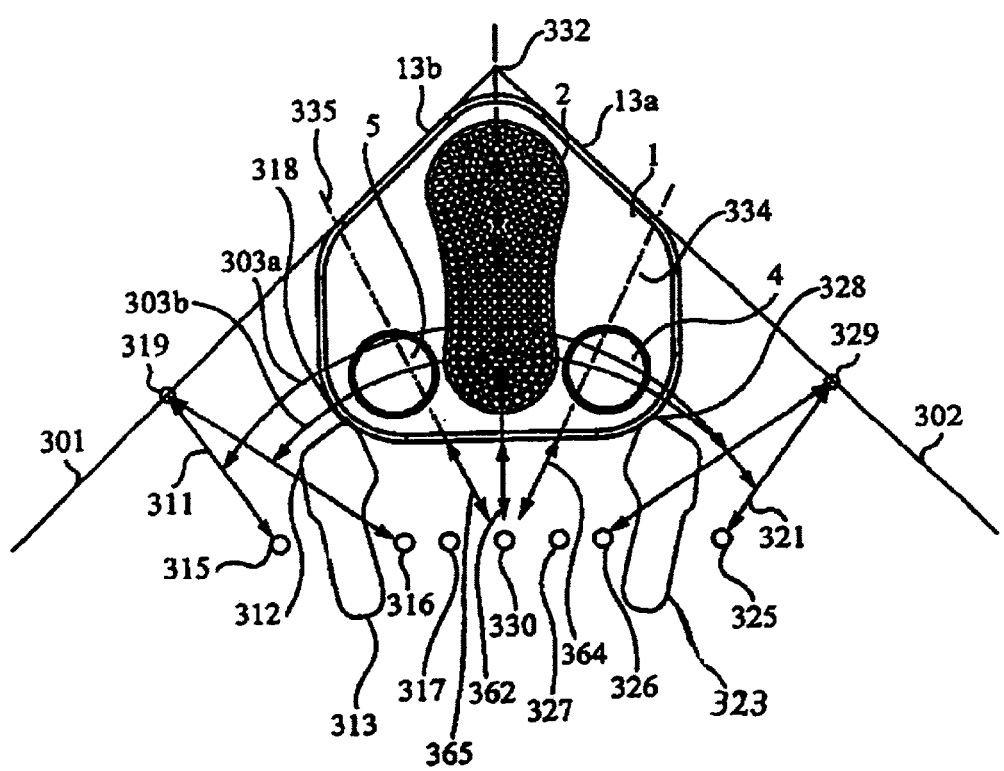

FIG. 3 shows a top down view of the ergonomic conditions for a user of the present invention.

Figure 4:
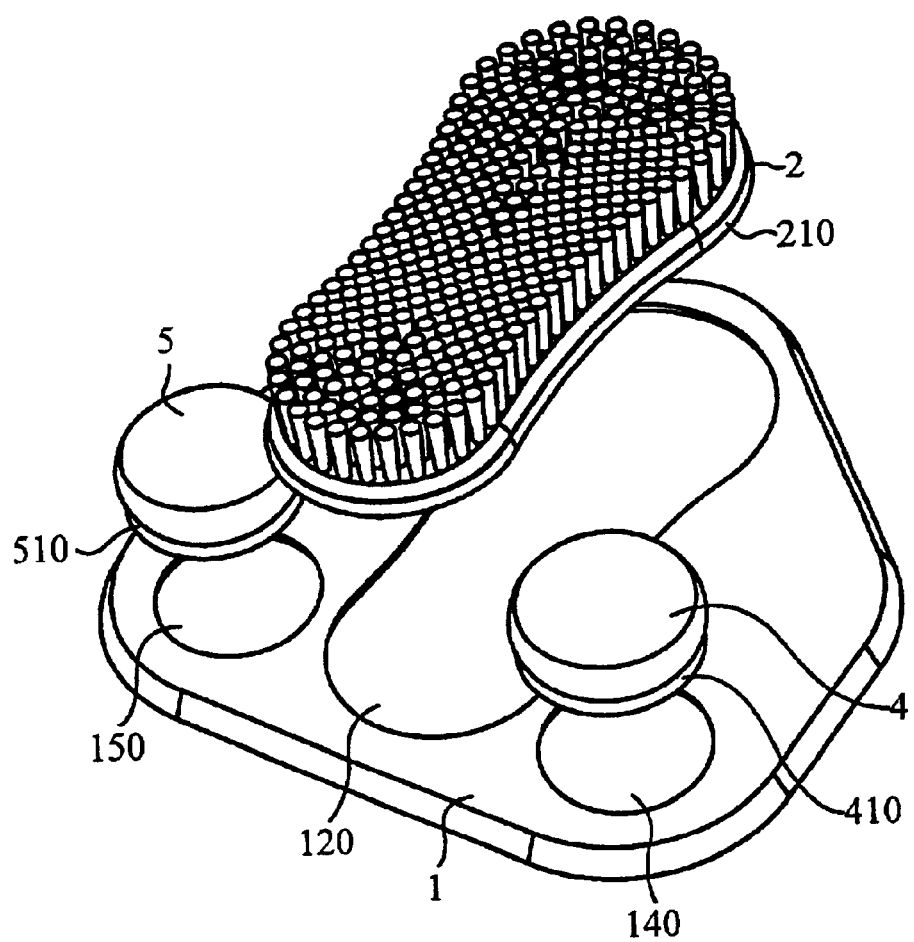

FIG. 4 shows a perspective view of the individual components of the present invention in exploded arrangement.

DETAILED DESCRIPTION

The bottom side of a person's foot requires typically extensive cleaning and care taking. In addition, portions of the sole of a person's foot are exposed to relatively high mechanical friction, which eventually results in increased growth of horny skin layers.

Unfortunately, a foot's bottom is hard to access such that chiropody is typically neglected. The present invention introduces a method and apparatus for ergonomic basic chiropody.

Basic chiropody typically includes the cleaning of the feet and the removing of horny skin layers. The cleaning is performed by wetting or soaking the feet, soaping, brushing, and rinsing them. The removing of the horny skin layers is accomplished by scrubbing them with pumice or any other scrubbing device. Wetting or soaking of the feet is typically accomplished without a physical effort by either stepping into a bath or showering the feet. Soaping, brushing and scrubbing require the person to get into a stable position such that one foot at a time can be brought into reach of the hands. Usually a person is sitting down to stabilize itself. Even in a sitting position, it is difficult to access the soles of the feet. The person has to maintain a certain twisted position while performing movements with a brush or a scrubber along the sole of the foot.

In cases where limited space does not allow for comfortable sitting, a stable position becomes even more difficult to maintain while accessing a foot. This applies mainly to shower cabins, which are conventionally dimensioned such that sitting in them is not easy or even impossible. In addition, the floor of shower cabins is covered during use with a mixture of water and soap. This makes the floor of the shower cabin slippery. As a result, foot cleaning in shower cabins is unsafe and difficult to accomplish.

Figure 1:
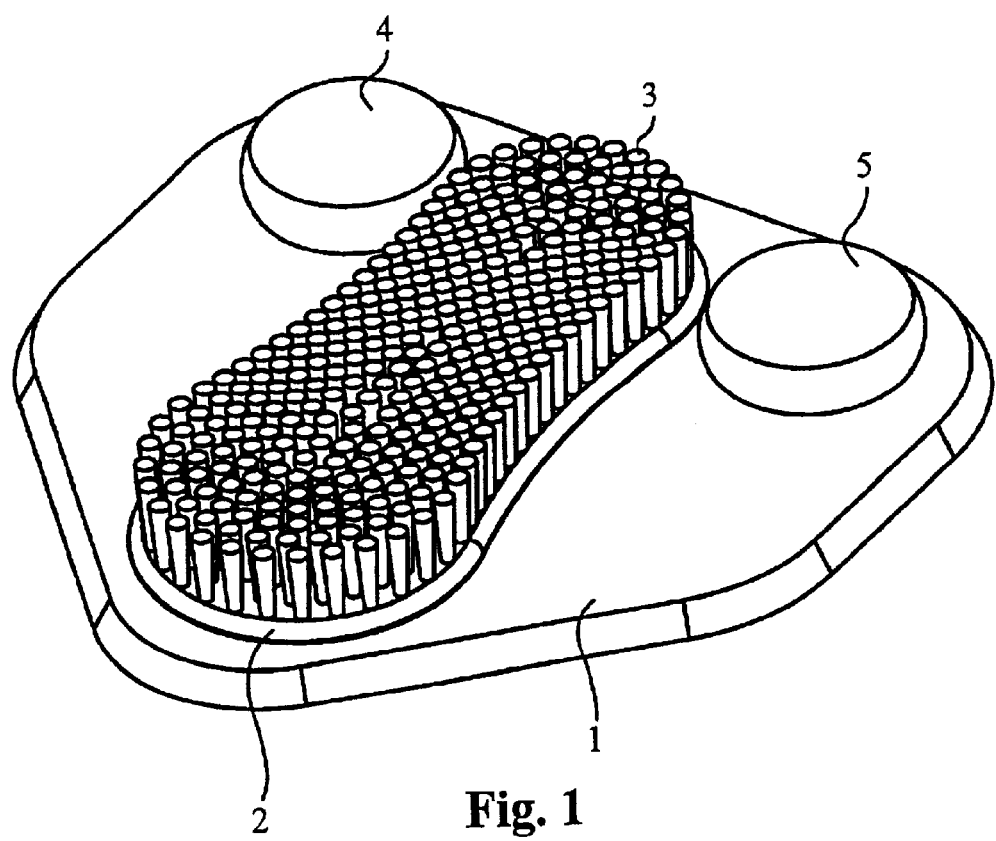
FIG. 1 shows a perspective view of an exemplary configuration of the present invention.

FIG. 1 shows a preferred embodiment of the present invention. On a base plate 1 are removable fixated a brushing device 2, a soaping device 4 and a scrubbing device 5. The brushing device 2 has a number of brushing elements 3.

Brushing devices placed on the floor have typically the problem that the friction between brush and foot becomes higher than the friction between the brushing device and the floor. As a result, conventional foot brushing devices intend to slip back and forth. In the present invention the base plate 1 is shaped, such that it corresponds with a first base edge 13a (see FIG. 2) to a first wall element 302 (see FIG. 3) and with a second base edge 13b (see FIG. 2) to a second wall element 301 (see FIG. 3).

The placement of the apparatus in the corner between first and second wall elements 301 and 302 defines the position and orientation of the apparatus.

Before the person begins to use the apparatus, the person positions itself in front of the apparatus such that the foot, which is meant to carry the person's weight, touches the back end of the base plate 1. The person's orientation is thereby in direction of the corner between first and second wall element 301 and 302. This specific orientation allows the person to stabilize itself by pressing with the hands against the first and second wall elements 301 and 302. Typically, first and second wall elements 301 and 302 are perpendicular like, for example, in the corner of a shower cabin or in the corner of a conventional bathroom.

FIG. 3 shows a top down view of the apparatus positioned in the corner between first and second wall elements 301 and 302. The contacting of the first base wedge edge 13a with the second wall element 302 and the contacting of the second base wedge edge 13b with the first wall element 301 define the position of the apparatus and the orientation of the main operation axis 332. Brushing device 2, soaping device 4 and scrubbing device 5 are shaped and positioned on the base plate 1 within an essentially triangular area. As a result, the base plate 1 itself may be contacting the first and second wall elements 301 and 302 without the first and second wall elements 301 and 302 hampering the access of the devices 2, 4, 5 by a foot to be cleaned. As a further result, the main operation axis 332 is also the symmetry axis of the first and second wall elements 301, 302.

After a person has soaked or wetted his or her foot or feet, the person positions itself at the back end of the base plate 1 such that the active foot, which is meant to utilize the apparatus, comes to rest with its active foot center 330 approximately above the main operation axis 332 of the apparatus. The active foot is either the right or the left foot. In case the right foot is the active foot, the person supports his or her weight on the left foot shown in the FIG. 3 with the left resting foot contour 313. For this case, the person's body center is in the approximate position shown by the first body center point 317. In addition, the left shoulder joint of the person is approximately in the position shown by the first left shoulder point 315. Further, the right shoulder joint of the person is approximately in the position shown by the first right shoulder point 326.

In case the left foot is the active foot, the person holds his or her weight with the right foot shown in the FIG. 3 with the right resting foot contour 323. For this case, the persons body center is in an approximate position shown by the second body center point 327. In addition, the left shoulder joint of the person is approximately in a position shown by the second left shoulder point 316. Further, the right shoulder joint of the person is approximately in a position shown by the second right shoulder point 325.

The person utilizes the soaping device 4 by moving the active foot essentially along the soaping direction 334. The person utilizes the brushing device 2 by moving the active foot essentially along the main operation axis 332. The person utilizes the scrubbing device 5 by moving the active foot essentially along the scrubbing direction 335.

The person may pivot the active foot around its ankle to contact specific areas of the active foot with the corresponding device 2, 4, 5.

Soaping device 4, scrubbing device 5 and brushing device 2 are positioned such that the soaping direction 334 and the scrubbing direction 335 are in a predetermined angular offset to the main operation direction 332. The predetermined angular offset is within an angular flexibility range of the persons physiognomy such that the soaping device 4 and the scrubbing device 5 can be accessed by the active foot without forcing the person to change the orientation and/or position of the resting foot. In the preferred embodiment, there is a selected maximum angular offset.

The main operating direction 332 corresponds with a physiognomic axis. The physiognomic axis represents the direction, in which the foot can be moved in the most natural way, as it occurs, for instance during walking or during running. In this way, the use of the apparatus is accomplished with a minimum of physical effort.

All back and forth movements have to overcome friction resistance between the devices and the active foot. The force that has to be applied by the person in order to overcome this friction resistance causes resulting force vectors 365, 364 and 362. First and second base wedge edges 13A, 13B preferably extend beyond the force vectors 364, 365 in order to prevent a resulting twisting momentum of the apparatus.

The position of the person in a corner between first and second wall element 301 and 302 allows the person to stabilize itself in an advantageous ergonomic way by pushing against first and second wall elements 301 and 302. The person contacts and/or holds with the left hand approximately at a position shown with the left wall contact 319. The person contacts and/or holds itself with the right hand approximately at a position shown with the right wall contact 329. The person may push against the plain wall or at.specifically placed holding devices.

In case the person's right foot is the active foot, a first left stabilizing vector 311 is defined between the first left shoulder point 315 and the left wall contact 319 by the persons fixating left arm. In addition, a first right stabilizing vector 321 is defined between the first right shoulder point 326 and the right wall contact 329 by the persons rigid held right arm.

In case the persons left foot is the active foot, a second left stabilizing vector 312 is defined between the second left shoulder point 316 and the left wall contact 319 by the persons fixating left arm. In addition, a second right stabilizing vector 321 is defined between the second right shoulder point 325 and the right wall contact 329 by the persons fixating right arm.

Since the first and second wall element 301 and 302 are in a typically angle of 90 degrees, the stabilizing vectors are of ergonomically advantageous short length. In addition, the first and second left stabilizing vectors 311 and 312 define together with the first and second right stabilizing vectors 322 and 321 a first and second stabilizing angle 303a and 303b.

The stabilizing vectors 311,312,322 and 321 define together with resulting force vectors 362,364 and 365 force triangles. These force triangles assure a stable stand of the person during the basic chiropody.

The resting foot contacts the base plate 1 on the base edge 13C. In case, the resting foot is the left foot the contacting point is at an approximate position shown by the left fixating point 318. In case, the resting foot is the right foot the contacting point is at an approximate position shown by the right fixating point 328. The fixating point 318 e.g. 328 is the third position definition element together with the contacting first and second base edges 13a and 13b. As a result, the apparatus is fully defined in position and orientation such that it does not move regardless of the forces imposed on it by the active foot.

The bottom side of a foot has typically a number of concave and convex features. To access all these features, the soaping device 4, the scrubbing device 5 and the brushing device 2 are preferably specifically shaped. FIG. AA shows in that context a sectional view of the inventive apparatus along a section line A—A indicated in FIG. 2. FIG. AA shows the soaping device profile 42 and the scrubbing device profile 52, which have a profile curvature and a free access height 41 and 51 such that all features of a sole can be brought into contact with the devices.

The scrubbing device 5 is preferably made from pumice. The rigid nature of the scrubbing device 5 requires it to have a scrubbing device contour 53 (see FIG. 2), which has a contour curvature that creates together with its profile curvature a first shape. The first shape assures the access of the horny skin regions of the foot during the regular use of the apparatus.

The soaping device 4 is preferably made from soap, which is also inflexible. The rigid nature of the soaping device 5 requires it to have a soaping device contour 43 (see FIG. 2), which has a contour curvature that creates together with its profile curvature a second shape. The second shape assures the access of all regions of the foot to apply soap during the regular use of the apparatus.

The brushing device 2 consists mainly of the brushing elements 3, which define together the flexible brushing body. The brushing elements have a brushing surface 32, which is shown in the FIG. AA as being planar. It is noted, that the brushing surface 32 may have any shaped brushing surface 32 that is suitable to reach all regions of a sole and regions between the toes. The brushing surface 32 may be continuously shaped or with interruptions of individually shaped and lengthened brushing elements 3.

The flexible and resilient nature of the brushing elements 3 result in a brushing device contour 23 that is a multitude of the soaping device contour 43 e.g. the scrubbing device contour 53. The extended area of the brushing device 2 reduces the average pressure that is applied on each brushing element 3. As a result, the brushing elements 3 can be made of a softer material compared to small sized foot brushes. The soft material of the brushing elements 3 provides a better fit to the shape of a foot's bottom. Furthermore, the soft material enhances the comfort with which the brushing device 2 can be used.

The brushing device contour 23 defines together with the brushing surface 32 a third shape. The third shape assures the access of all relevant foot areas during the regular use of the apparatus.

The soaping device 4 and the scrubbing device 5 are fixated in positions on the base plate 1, which are at a maximum distance to the first and second base edge 13a and 13b. Hence, the use of the soaping device 4 and the scrubbing device 5 by the active foot is not limited by first and second wall 301 and 302.

The brushing device 2 is fixated in a position on the base plate 1, such that it takes advantage of the full length of the base plate 1. The soaping device 4, the scrubbing device 5 and the brushing device 2 are positioned relative to each other, such that the base plate 1 is able to fixate them without exceeding the space typically available for permanent placement in a shower cabin and/or in a bathroom.

Soaping device 4, scrubbing device 5 and brushing device 2 are disposable parts of the apparatus. FIG. AA shows them with clamping contours 211, 411 and 511 that define the clamping features 210, 410 and 510 (see FIG. 4). The clamping features 210, 410 and 510 are essentially protrusions of the correlated brushing device contour 23, the soaping device contour 43 and the scrubbing device contour 53. The protrusions expand with increasing depth such that they interlock with the corresponding cavities 120, 140 and 150 (see FIG. 4) of the base plate 1. During the assembly and disassembly, each individual device is pressed into e.g. pressed out of its corresponding cavity.

The base plate 1 is made of elastic material to allow a resilient deformation of the cavities during the assembly e.g. disassembly. As a result, the devices may have varying properties and characteristics and can be combined within the apparatus to adjust to individual needs for basic chiropody.

The free positioning of each device further improves the cleaning of the apparatus.

It is noted, that the scope of the invention is not limited to combined soaping, brushing and/or scrubbing feet but extends to cases where soaping, brushing and/or scrubbing is provided solely or in combination with only one other operation. The scope of the invention further extends to any activities during which a person has to stand on a single foot and has to move the other food along a device. Such activities may include shoe cleaning, foot bathing, foot massaging, and any other mechanical, electrical and/or magnetic treatment induced on a human's foot.

Accordingly, the scope of the present invention described in the specification above is set forth by the following claims and their legal equivalent.

What is claimed is:

1. A chiropody apparatus for being positioned and being operated on a floor and in a corner region defined by a first wall element and a second wall element, said apparatus comprising:
   a. a base having a first base edge and a second base edge correspondingly shaped to said corner region and holding a number of chiropody devices in the vicinity of a main operation direction of said chiropody apparatus;
   b. wherein said main operation direction is corresponding to a symmetry axis of said first wall element and said second wall element;
   c. wherein said base has a clamping means removably holding at least one of said number of chiropody devices thereto; and
   d. wherein said at least one of said number of chiropody devices has a fixture correspondingly shaped to said clamping means.

2. The chiropody apparatus of claim 1, wherein said number of chiropody devices include a brushing device, a soaping device and a scrubbing device.

3. The chiropody apparatus of claim 1, wherein said soaping device and said scrubbing device have a rotationally symmetric shape and are symmetrically fixated on said base relative to said main operation direction and wherein said brushing device is fixated along said main operation direction.

4. A chiropody apparatus for being positioned and being operated on a floor and in a corner region defined by a first wall element and a second wall element, said apparatus comprising a fixating base holding a scrubbing device, a soaping device and a brushing device wherein
   said scrubbing device, said soaping device and said brushing device define an essentially triangular area within said fixating base and wherein said fixating base is shaped to fit into said corner region with a main operation direction of said chiropody apparatus being essentially identical with a symmetry axis of said first wall element and said second wall element.

5. The chiropody apparatus of claim 1, wherein:
   a. said fixating base has a clamping means removably holding at least one of said scrubbing device, said clamping device and said brushing device; and
   b. said at least one of said scrubbing device, said clamping device and said brushing device has a fixture correspondingly shaped to said clamping means.

\* \* \* \* \*